(12) United States Patent
Satyanarayana et al.

(10) Patent No.: US 8,367,832 B2
(45) Date of Patent: Feb. 5, 2013

(54) CRYSTALLINE FORMS OF NELFINAVIR MESYLATE

(75) Inventors: Chava Satyanarayana, Secunderabad (IN); Vasireddy Umamaheswara-Rao, Secunderabad (IN); Vellanki Siva Ram Prasad, Hyderabad (IN); Balusu Rajababu, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 1001 days.

(21) Appl. No.: 11/791,557

(22) PCT Filed: Aug. 23, 2004

(86) PCT No.: PCT/IN2004/000255
§ 371 (c)(1),
(2), (4) Date: Feb. 29, 2008

(87) PCT Pub. No.: WO2006/021964
PCT Pub. Date: Mar. 2, 2006

(65) Prior Publication Data
US 2008/0312445 A1    Dec. 18, 2008

(51) Int. Cl.
*C07D 217/12*    (2006.01)
(52) U.S. Cl. .................................................. 546/146
(58) Field of Classification Search .............. 546/146; 514/307
See application file for complete search history.

(56) References Cited

U.S. PATENT DOCUMENTS 5,484,926 A * 1/1996 Dressman et al. ............ 546/114
5,962,725 A * 10/1999 Deason et al. ................ 560/130

FOREIGN PATENT DOCUMENTS

EP    0 984 000 A1    3/2000

OTHER PUBLICATIONS

Chemical & Engineering News, Feb. 2003, 32-35.*
Brittain ed., "Polymorphism, etc.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Bernstein et al., "Polymorphism in Moleular Crystals", Oxford: Clarendon Press, 2002, pp. 117, 118, 272 and 273.*
Davidovich et al., "Detection of Polymorphism, etc.," American Pharmaceutical Review, IN: Russell Pub., 2004, 7(1), pp. 10, 12, 14, 16 and 100.*
Longer et al; Preformulation Studies of a Noval HIV Protease Inhibitor, AG1343; 84 Journal of Pharm. Sciences No. 9 p. 1090-1093 (Sep. 1995).

* cited by examiner

*Primary Examiner* — Patricia Morris
(74) *Attorney, Agent, or Firm* — Ladas & Parry LLP

(57) ABSTRACT

The present invention provides novel crystalline forms of Nelfinavir mesylate, Form-A, Form-B, Form-C, Form-D and the process for their preparation without the use of any special equipment such as a spray drier, avoiding the use of highly flammable solvents such as ethers. The crystalline form can be tailored with the selection of the ante solvent and appropriate conditions for the process.

4 Claims, 5 Drawing Sheets

CRYSTALLINE FORMS OF NELFINAVIR MESYLATE

The present invention relates to novel crystalline forms of Nelfinavir mesylate and the process for their preparation.

BACKGROUND OF THE INVENTION

Nelfinavir mesylate, namely [3S-(3R,4aR,8aR,2'S,3'S)]-2-{2'-hydroxy-3'-[(phenylthio)methyl]-4'-aza-5'-oxo-5'-(2"-methyl-3"-hydroxy phenyl)pentyl}decahydroiso-quinoline-3-N-tertbutylcarboxamide mesylate has the formula

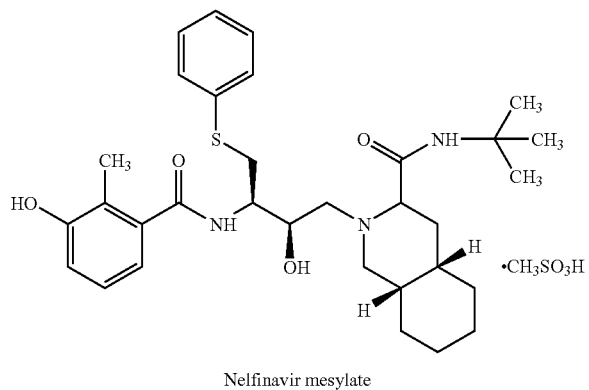

Nelfinavir mesylate

Nelfinavir mesylate is a HIV-protease inhibitor designed using protein structure-based techniques and has shown to be effective in treatment of the HIV-infected individuals. Treatment of HIV-infected individuals is one of the most pressing biomedical problems of recent times. A promising new therapy has emerged as an important method for preventing or inhibiting the rapid proliferation of the virus in human tissue. HIV-protease inhibitors block the a key enzymatic pathway in the virus, causing the replication of HIV virus to terminate resulting in substantially decreased viral loads, which slows the steady decay of the immune system and its resulting deleterious effects on human health.

U.S. Pat. No. 5,484,926 discloses Nelfinavir base, Nelfinavir mesylate and process for their preparation. The procedure disclosed for preparation of Nelfinavir mesylate is by dissolution of Nelfinavir base in a mixture of methanol, methylene chloride, drop wise addition of methanesulfonic acid solution in methylene chloride, concentration of the reaction mass to get crude salt as white foam, dissolution of crude salt in THF followed by addition to mixture of ethyl ether and hexane, isolation and drying in vacuum oven.

U.S. Pat. No. 5,962,725 discloses intermediate compounds, which can be used in several schemes for the preparation of Nelfinavir mesylate and also methods for making Nelfinavir mesylate from the Nelfinavir base. One of the procedures disclosed is the conversion of Nelfinavir base to Nelfinavir mesylate by spray drying in which the Nelfinavir base in organic solvent is mixed with an equivalent amount of methanesulfonic acid till Nelfinavir mesylate is formed and the resultant slurry or solution is pumped through a spray drier with controlled settings. U.S. Pat. No. 5,962,725 further discloses that the Nelfinavir mesylate is prepared by dissolving the Nelfinavir base in a suitable solvent (such as THF, methanol or ethanol), adding a molar equivalent of methanesulfonic acid, mixing to get a uniform solution and adding this solution rapidly to several volumes of an ante solvent (such as methyl tert-butyl ether, diethyl ether, hexane, heptane) with rapid stirring.

The process disclosed in U.S. Pat. No. 5,962,725 either involves the special equipment like spray drier or usage of highly flammable solvents such as ethers, for whose usage is risky in commercial level.

The U.S. Pat. No. 5,962,725 does not specify the solid nature of the product obtained. However Longer et al. in Journal of Pharmaceutical Sciences, Volume 84 (1995) page 1090-1093, discloses the XRD, DSC and TGA studies along with other physiochemical properties of Nelfinavir mesylate to establish a preformulation database. Based on XRD (FIG. 1), it further reveals that Nelfinavir mesylate is substantially amorphous with no evidence of long-range periodicity. It further reveals that there is no evidence of crystallinity by XRD and no birefringingence on polarized light microscopy after repeated heating and cooling cycles including samples stored under a variety of stressed conditions (e.g. 40° C./80% RH) for up to 1 year.

Generally amorphous forms of drugs are hygroscopic thereby making them unsuitable for formulations. There is a long need of the industry for a stable crystalline forms of Nelfinavir mesylate that are less or not hygroscopic.

SUMMARY OF THE INVENTION

The main object of the present invention is to provide novel crystalline forms of Nelfinavir mesylate Another object of the invention is to provide a process for preparation of novel crystalline forms of Nelfinavir mesylate without involving the special equipment such as spray drier.

Another object of the invention is to provide finger printing for the novel crystalline forms of Nelfinavir mesylate by XRD, DSC and FTIR spectral data Accordingly, the present invention relates to novel crystalline forms, process for preparation of Nelfinavir mesylate starting from Nelfinavir base. The process comprises steps of dissolution of Nelfinavir base in organic solvent by addition of methanesulfonic acid, maintaining the reaction mass at selective temperature, cooling, followed by addition of ketone as an ante solvent to the clear solution then mixing, separating and drying to produce the novel crystalline forms of Nelfinavir mesylate.

The crystalline form of Nelfinavir mesylate produced depends on the ketone used as ante solvent. Acetone as an ante solvent produces Form-A; methyl ethyl ketone produces Form-B; methyl isobutyl ketone produces Form-C and 2-Pentanone produces Form-D. All the invented crystalline Nelfinavir mesylate forms exhibits typical x-ray diffraction patters as depicted in FIG. 2 to FIG. 5.

DETAILED DESCRIPTION OF THE INVENTION

Figure 1:
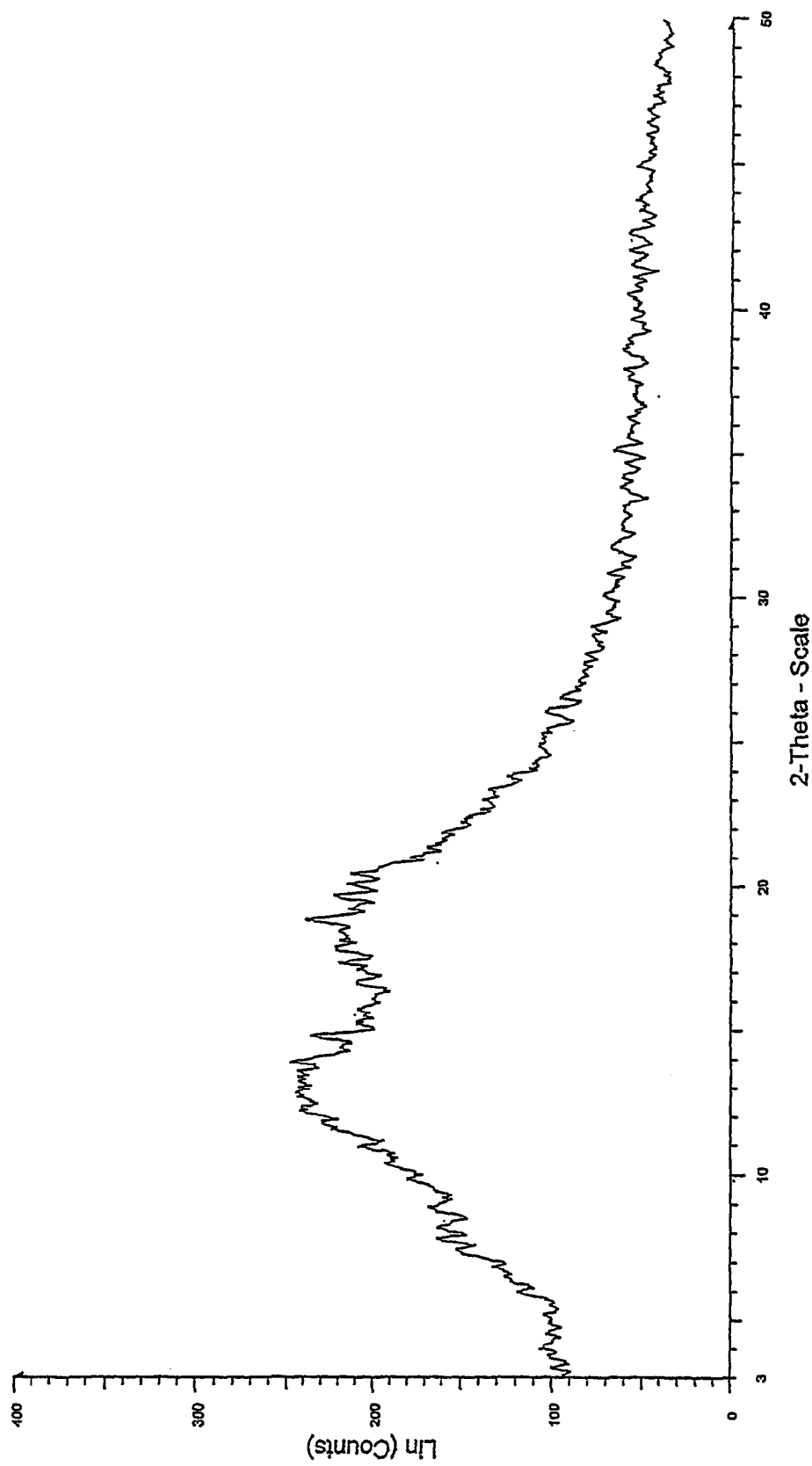
FIG. 1 XRD pattern of the Nelfinavir mesylate of the reference substance

The preparation of novel crystalline forms of Nelfinavir mesylate designated as Form-A, Form-B, Form-C, Form-D comprises of the following steps Suspending the Nelfinavir base in organic solvent
Adding methanesulfonic acid
Mixing the reaction mass to obtain a solution
Cooling the reaction mass to 10° C. to 35° C.

Adding an ante solvent slowly over 15 min to 4 hrs

Mixing the reaction mass for about 30 min to 6 hrs

Separating and drying the crystalline Nelfinavir mesylate

The invented novel crystalline Nelfinavir mesylate Form-A, Form-B, Form-C & Form-D are anhydrous and are characterized by X-ray diffraction pattern and IR spectral data.

Thus in accordance to the present invention Nelfinavir base is suspended in an organic solvent, selected from methanol, ethanol, isopropanol, THF, and methanesulfonic acid is added at temperature below 45° C. over a period of 10 min to 4 hrs. The reaction mass is mixed for about 15 min to 4 hrs to form a solution and then cooled to 10° C. to 35° C. A ketone such as acetone, methyl ethyl ketone, methyl isobutyl ketone, 2-pentanone is added as ante solvent at temperature 10° C. to about 35° C. in about 15 min to 4 hrs. The resulting reaction mass is maintained at temperature of 10° C. to 35° C. for about 30 min to 6 hrs then cooled and maintained at temperature of −10° C. to 15° C. for about 30 min to 4 hrs. The precipitated solid is separated and dried at temperature of 50° C. to 120° C., preferably at 80° C. to 110° C. under reduced pressure to produce novel crystalline forms of Nelfinavir mesylate.

The invention is now illustrated with a few non-limiting examples.

EXAMPLES

Example-I

Preparation of Crystalline Nelfinavir Mesylate Form-A

Nelfinavir base (15 g) is suspended in methanol (22.5 ml), and methanesulfonic acid (2.55 g) is added at temperature below 45° C. over 30 min. The reaction mixture is maintained at 40° C. to 45° C. for 1 hr to get clear solution. The obtained clear solution is cooled to a temperature of 25° C. to 30° C., acetone (87 ml) is added over 30 min and mixed for 2 hrs at 25° C. to 30° C. The reaction mass is cooled to 0° C. to 5° C. and maintained for 2 hrs. The precipitated solid is filtered, washed with chilled acetone (7.5 ml) and dried at 90° C. to 100° C. under vacuum till becomes constant weight.

Out put: 10 g (57% of the theoretical)

Figure 2:
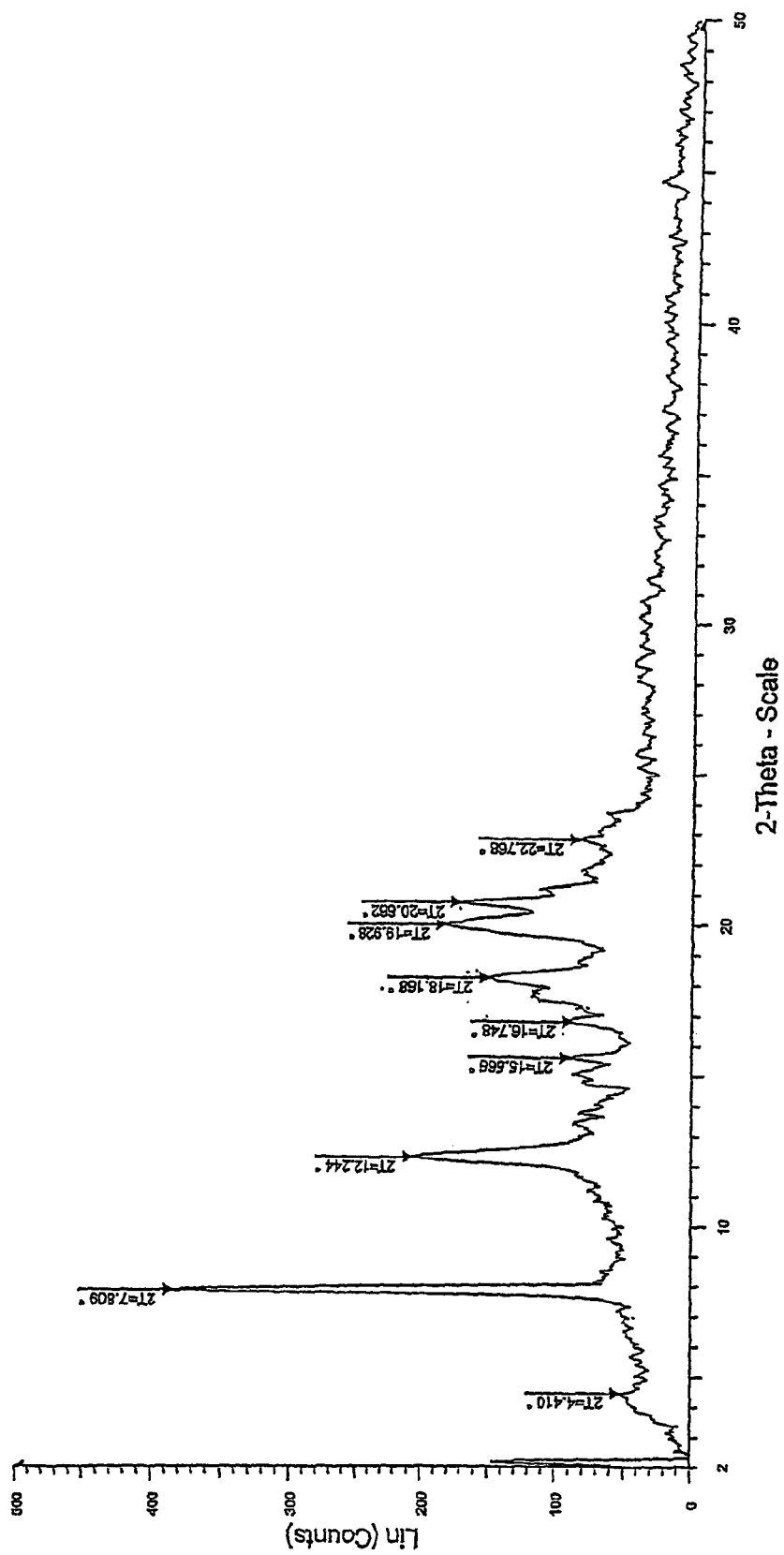
FIG. 2 XRD pattern of the crystalline Nelfinavir mesylate Form-A

The x-ray diffraction pattern of the product is as given in FIG. 2

Similarly Nelfinavir mesylate Form-A can be prepared by using ethanol, isopropanol, THF instead of methanol with the same procedure as described in example-I.

Example-II

Preparation of Nelfinavir Mesylate Form-B

Nelfinavir base (25 g) is suspended in THF (75 ml), and methanesulfonic acid (4.25 g) is added at temperature below 45° C. over 30 min. The reaction mixture is maintained at 40° C. to 45° C. for 1 hr to get clear solution. The obtained clear solution is cooled to 28° C. to 30° C. and methyl ethyl ketone (145 ml) is added over 20 min, mixed at temperature of 25° C. to 30° C. for 2 hrs. The reaction mass is cooled and maintained at 0° C. to 5° C. for 2 hrs. The precipitated solid is filtered, washed with chilled methyl ethyl ketone (12.5 ml) and dried at 90° C. to 100° C. under vacuum till becomes constant weight.

Out put: 20 g (68.6% of the theoretical)

Figure 3:
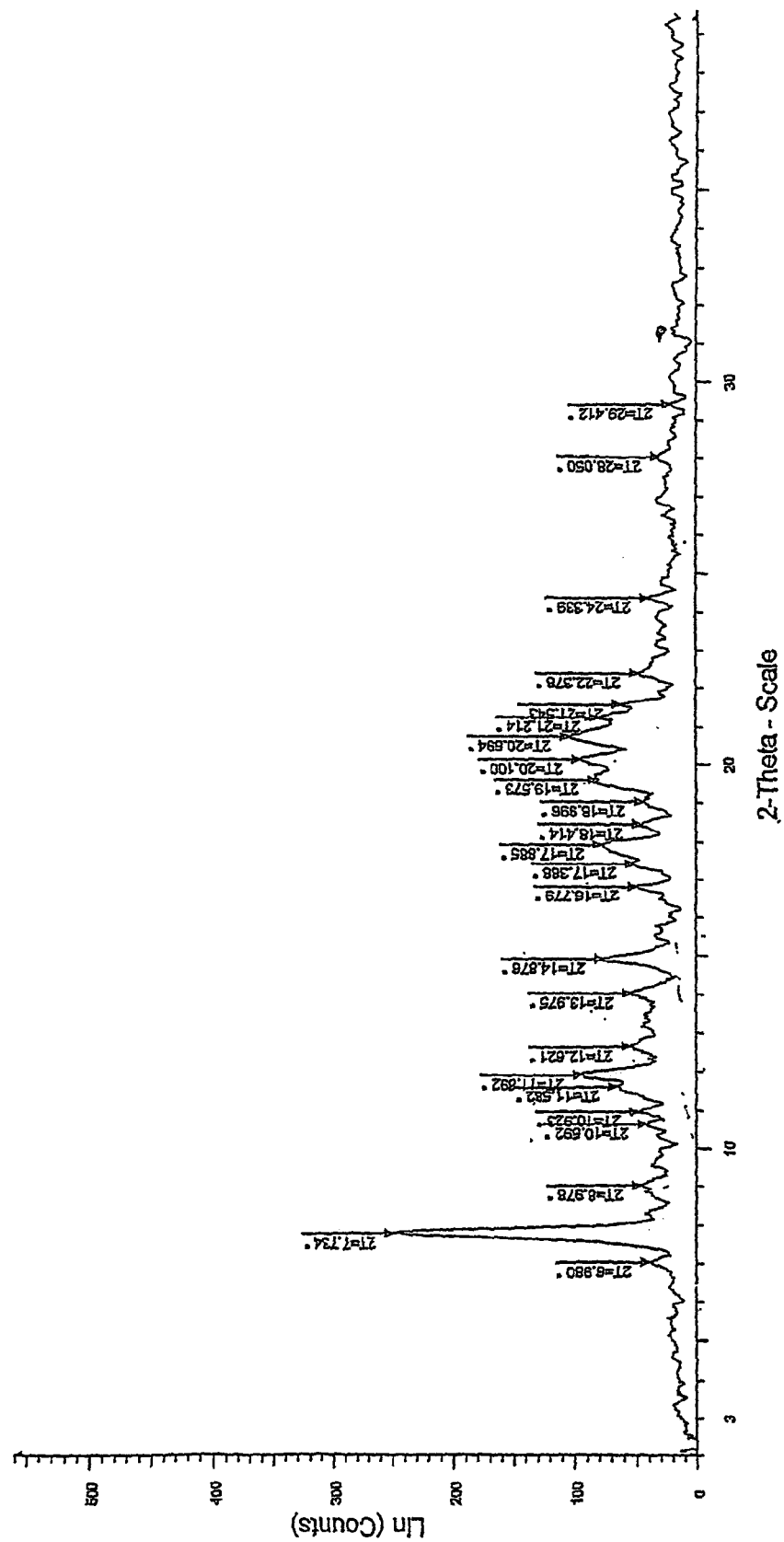
FIG. 3 XRD pattern of the crystalline Nelfinavir mesylate Form-B

The x-ray diffraction pattern of the product is as given in FIG. 3

Similarly Nelfinavir mesylate Form-B can be prepared by using methanol, ethanol and isopropanol, instead of THF with the same procedure as described in example-II.

Example-III

Preparation of Nelfinavir Mesylate Form-C

Nelfinavir base (20 g) is suspended in ethanol (30 ml), and methanesulfonic acid (3.4 g) is added at temperature of 28° C. to 45° C. over 20 min. The reaction mixture is maintained at 40° C. to 45° C. for 1 hr to get clear solution. The obtained clear solution is cooled to 28° C. to 30° C. and methyl isobutyl ketone (58 ml) is added over 30 min, mixed at temperature of 28° C. to 30° C. for 2 hrs. The reaction mass is cooled and maintained at 0° C. to 5° C. for 2 hr. The precipitated solid is filtered, washed with chilled methyl isobutyl ketone (10 ml) and dried at 90° C. to 100° C. under vacuum till becomes constant weight.

Out put: 18 g (77% of the theoretical)

Figure 4:
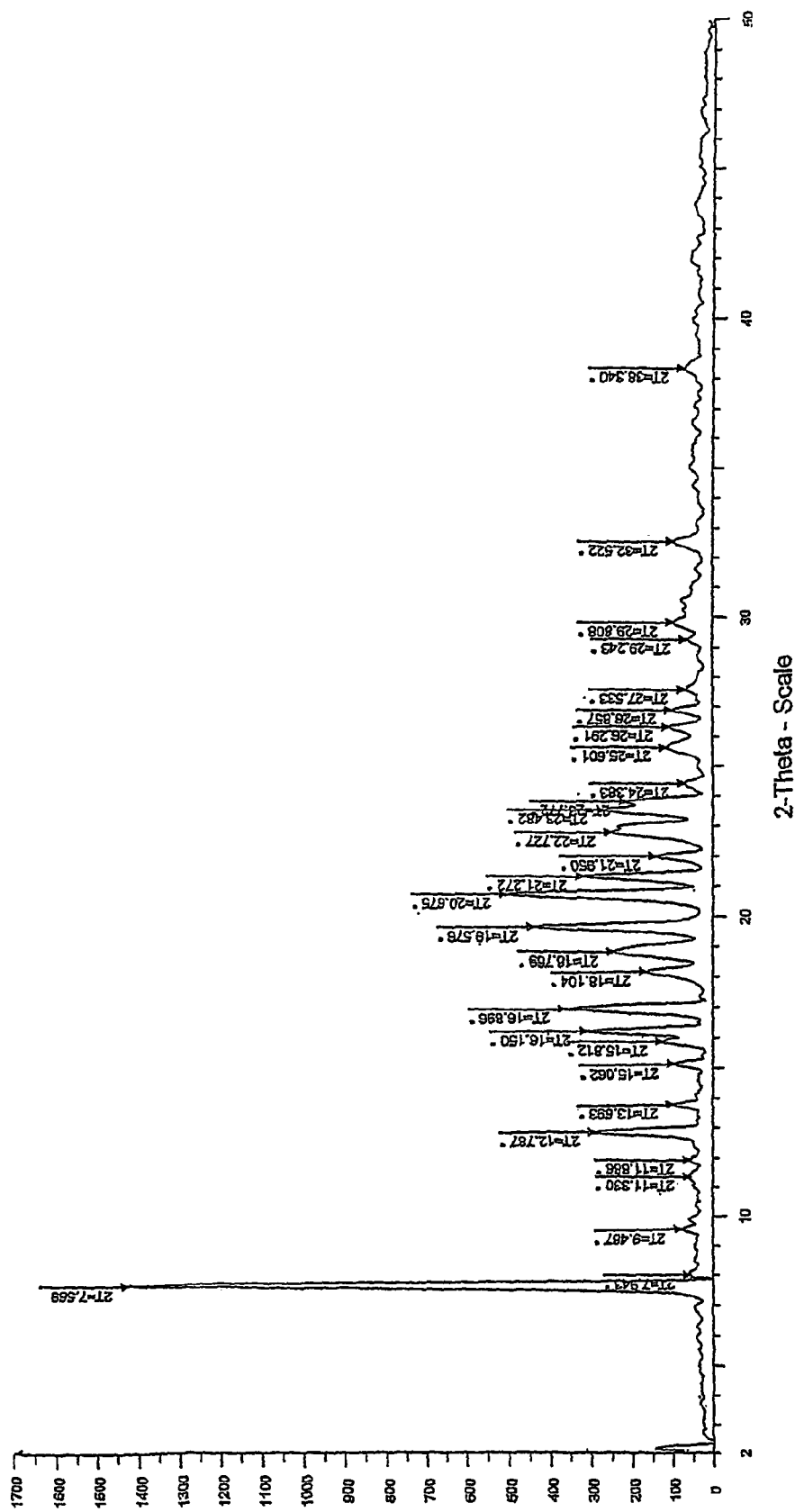
FIG. 4 XRD pattern of the crystalline Nelfinavir mesylate Form-C

The x-ray diffraction pattern of the product is as given in FIG. 4

Similarly Nelfinavir mesylate Form-C can be prepared by using methanol, isopropanol, THF instead of ethanol with the same procedure as described in example-III.

Example-IV

Preparation of Nelfinavir Mesylate Form-D

Nelfinavir base (25 g) is suspended in THF (75 ml), and methanesulfonic acid (4.25 g) is added at temperature of 26° C. to 40° C. over 30 min. The reaction mixture is maintained at 40° C. to 45° C. for 1 hr to get clear solution. The obtained clear solution is cooled to 28° C. to 32° C. and 2-pentanone (145 ml) is added over 30 min, mixed at temperature of 28° C. to 32° C. for 1 hrs. The reaction mass is cooled and maintained at 0° C. to 5° C. for 2 hr. The precipitated solid is filtered, washed with chilled 2-pentanone (12.5 ml) and dried at 90° C. to 100° C. under vacuum till becomes constant weight.

Out put: 20 g (68.4% of the theoretical)

Figure 5:
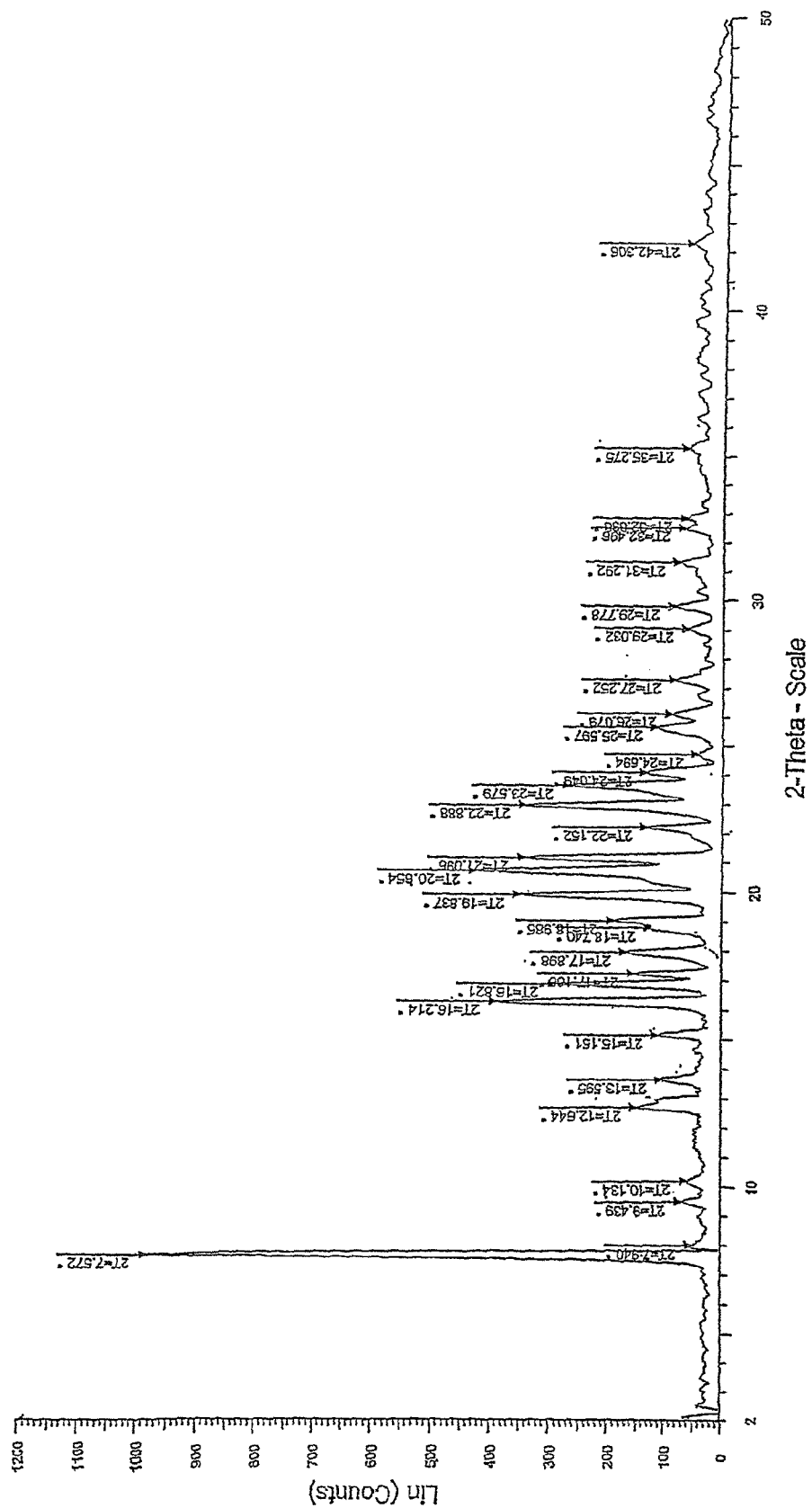
FIG. 5 XRD pattern of the crystalline Nelfinavir mesylate Form-D

The x-ray diffraction pattern of the product is as given in FIG. 5

Similarly Nelfinavir mesylate Form-D can be prepared by using methanol, ethanol and isopropanol instead of THF with the same procedure as described in example-IV.

We claim:

1. Crystalline Nelfinavir mesylate Form-A characterized by an x-ray diffraction pattern (XRD) as shown in FIG. 2 with 2θ values at 7.72, 12.23, 15.42, 17.41, 17.98, 19.81, 20.18, 21.78 and 24.70±0.2 deg.

2. A process for the preparation of crystalline Nelfinavir mesylate Form-A, comprising the steps of:
   a) suspending Nelfinavir base in an organic solvent;
   b) adding methane sulfonic acid at a temperature below 45° C.;
   c) cooling the resulting reaction mass to 10° to 35° C.;
   d) adding an antisolvent; and
   e) isolating crystalline Nelfinavir meslate Form-A.

3. The process according to claim 2, wherein the organic solvent is methanol, ethanol, iso-propanol or tetrahydrofuron.

4. The process according to claim 2, wherein the antisolvent is acetone, methyl ethyl ketone or methyl isobutyl ketone.

\* \* \* \* \*